US008084445B2

(12) United States Patent
Huq et al.

(10) Patent No.: US 8,084,445 B2
(45) Date of Patent: Dec. 27, 2011

(54) PHARMACEUTICAL FORMULATION

(75) Inventors: Abu S Huq, Plainsboro, NJ (US); Allan J Weingarten, Westfield, NJ (US); Robert D Simmons, Martinsville, NJ (US)

(73) Assignee: Schering-Plough Animal Health Corporation, Union, NJ (US)

( * ) Notice: Subject to any disclaimer, the term of this patent is extended or adjusted under 35 U.S.C. 154(b) by 813 days.

(21) Appl. No.: 11/201,044

(22) Filed: Aug. 10, 2005

(65) Prior Publication Data

US 2006/0122159 A1 Jun. 8, 2006

Related U.S. Application Data

(60) Provisional application No. 60/601,475, filed on Aug. 13, 2004.

(51) Int. Cl.
*A61K 31/58* (2006.01)
*A61K 31/496* (2006.01)
*A61K 31/4178* (2006.01)

(52) U.S. Cl. .................. 514/171; 514/254.07; 514/397; 514/253.08

(58) Field of Classification Search .................. 514/171, 514/253.08, 254.07, 397
See application file for complete search history.

(56) References Cited

U.S. PATENT DOCUMENTS

| | | | |
|---|---|---|---|
| 4,235,892 A | 11/1980 | Nagabhushan | |
| 4,311,857 A | 1/1982 | Nagabhushan | |
| 4,443,430 A | 4/1984 | Mattei et al. | |
| 4,582,918 A | 4/1986 | Nagabhushan et al. | |
| 4,743,700 A | 5/1988 | Jommi et al. | |
| 4,820,695 A | 4/1989 | Debono et al. | |
| 4,876,352 A | 10/1989 | Schumacher et al. | |
| 4,973,750 A | 11/1990 | Nagabhushan et al. | |
| 5,104,868 A | 4/1992 | McGuirk | |
| 5,105,009 A | 4/1992 | Jommi et al. | |
| 5,198,220 A | 3/1993 | Damani | |
| 5,227,494 A | 7/1993 | Schumacher et al. | |
| 5,242,910 A | 9/1993 | Damanj | |
| 5,352,832 A | 10/1994 | Wu et al. | |
| 5,382,673 A | 1/1995 | Clark et al. | |
| 5,491,139 A | 2/1996 | Demuth et al. | |
| 5,496,947 A | 3/1996 | Yoon et al. | |
| 5,498,615 A | 3/1996 | Kim et al. | |
| 5,530,116 A | 6/1996 | Demuth et al. | |
| 5,567,844 A | 10/1996 | Jommi et al. | |
| 5,646,163 A | 7/1997 | Demuth et al. | |
| 5,661,151 A | 8/1997 | Saksena et al. | |
| 5,663,361 A | 9/1997 | Towson et al. | |
| 5,672,600 A | 9/1997 | Demuth et al. | |
| 5,770,597 A | 6/1998 | Kim et al. | |
| 5,834,472 A | 11/1998 | Sangekar et al. | |
| 5,840,333 A | 11/1998 | Gousset et al. | |
| 5,846,971 A | 12/1998 | Sangekar et al. | |
| 2002/0037877 A1* | 3/2002 | Singh | 514/78 |
| 2003/0064939 A1 | 4/2003 | Sklavounos et al. | |
| 2003/0153516 A1 | 8/2003 | Ponikau et al. | |
| 2010/0087409 A1 | 4/2010 | Freehauf et al. | |

FOREIGN PATENT DOCUMENTS

| | | |
|---|---|---|
| JP | 10109928 A | 4/1998 |
| WO | WO 96/16055 | 5/1996 |
| WO | WO 00/15234 A | 3/2000 |
| WO | 0189495 A2 | 11/2001 |
| WO | WO 03/026671 A | 4/2003 |
| WO | WO 2005/077360 A | 8/2005 |

OTHER PUBLICATIONS

Kumar et al., "Treatment of Otitis Externa in Dogs Associated with *Malassezia pachydermatis*", Indian Vet. J., Jul. 2002, pp. 727-729, vol. 79, No. 7, XP008044549.
International Search Report for International Application No. PCT/US2005/028379.
Full English Translation of JP 10-109928 US—20 Pages.
Ghubash et al, "Evaluation of Adrenal Function in Small-Breed Dogs Receiving Otic Glucocorticoids", Vetinary Dermatology, No. 25, pp. 363-368 (2004).
Moriello et al, "Adrenocortical Suppression Associated with topical Otic Administration of Glucocorticoids in Dogs", JAVMA, vol. 193, No. 3, pp. 329-331 (1988).
Prakash et al, "Topical Mometasone—A Review of its pharmacological Properties and Therapeutic Use in the Treatment of Dermatological Disorders", Drugs, vol. 55, No. 1, pp. 145-163 (1998).
Reeder et al, "Comparative Adrenocortical Suppression in Dogs with Otitis Externa Following Topical Otic Administration of Four Different Glucocorticoid-Containing Medications", Veterinary Therapeutics, vol. 9, No. 2, pp. 111-121 (2008).
Schafer et al, "Novel Fluorine-Containing Analogs of Chloramphenicol and Thiamphenicol: Antibacterial and Biological Properties", Current Chemotherapy and Infectious Disease Proceedings of the 11u$^{th}$ICC and the 19$^{th}$ ICAAC American Society of Microbiology, pp. 444-446 (1980).
Zenoble et al, "Adrenocortical Suppression by Topically Applied Corticosteroids in Healthy Dogs", JAVMA, vol. 191, No. 6 (1987).

* cited by examiner

*Primary Examiner* — Sreeni Padmanabhan
*Assistant Examiner* — Sahar Javanmard
(74) *Attorney, Agent, or Firm* — William M. Blackstone; Kiera A. Mathey

(57) ABSTRACT

Disclosed are novel formulations for the treatment of otic infections in an animal comprising a triazole anti-fungal compound, a quinolone antibiotic and a corticosteroid such as mometasone furoate monohydrate.

10 Claims, No Drawings

PHARMACEUTICAL FORMULATION

CROSS-REFERENCE TO RELATED APPLICATION

This application claims benefit of priority to U.S. Provisional Patent Application Ser. No. 60/601,475, filed Aug. 13, 2004, which is incorporated by reference.

BACKGROUND OF THE INVENTION

All references cited herein are hereby incorporated in their entirety by reference. Otomax® Otic Suspension contains Gentamicin Sulfate, USP, Betamethasone Valerate, USP and Clotrimazole, USP. Mometamax® Otic Suspension contains Gentamicin Sulfate, USP, Clotrimazole, USP and Mometasone Furoate Monohydrate.

A problem with these products exists with regards to the potential for ototoxicity due to the aminoglycosides that are often used in such products. Accordingly, there exists a need for new combination products for the treatment of infections in animals that do not suffer from these infirmities.

SUMMARY OF THE INVENTION

Accordingly, there are disclosed pharmaceutical compositions for the treatment of an infection in an animal comprising Orbifloxacin or one of its pharmaceutically acceptable salts; an antifungally effective amount of the compound represented by the chemical structural formula I comprising:

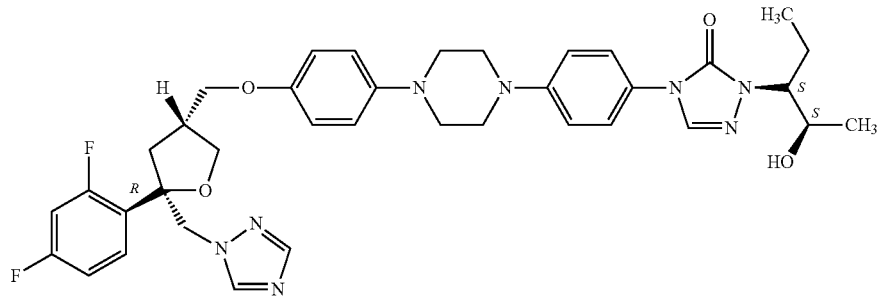

Mometasone Furoate Monohydrate and at least one pharmaceutically acceptable carrier, wherein said composition is a suspension.

Also disclosed are pharmaceutical compositions for the treatment of an infection in an animal comprising Orbifloxacin or one of its pharmaceutically acceptable salts; an antifungally effective amount of a pharmaceutically acceptable triazole compound, Mometasone Furoate Monohydrate and at least one pharmaceutically acceptable carrier, wherein said composition is a suspension.

DETAILED DESCRIPTION OF THE INVENTION

The present invention is directed to a pharmaceutical composition for the treatment of an infection in an animal comprising Orbifloxacin or one of its pharmaceutically acceptable salts; an antifungally effective amount of the compound represented by the chemical structural formula I comprising:

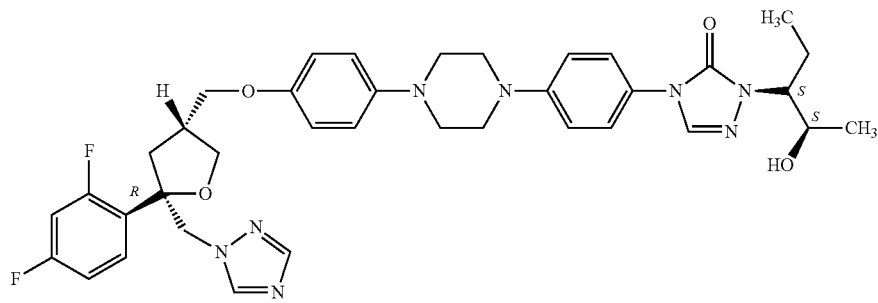

Mometasone Furoate Monohydrate and a pharmaceutically acceptable carrier, wherein the composition is a suspension.

Mometasone Furoate Monohydrate is a synthetic steroid hormone in the glucocorticoid family. Glucocorticoid hormones are potent anti-inflammatory agents. It also shows antipruritic and vasoconstrictive actions. It is used topically in the treatment of corticosteroid-responsive dermatoses such as psoriasis and atopic dermatitis. Mometasone Furoate, the active component of ELOCON® lotion, cream, and ointment, is an anti-inflammatory corticosteroid having the chemical name, 9,21-Dichloro-11 (beta), 17-dihydroxy-16 (alpha)-methylpregna-1,4-diene-3,20-dione 17-(2 Furoate). It is practically insoluble in water; slightly soluble in methanol, ethanol, and isopropanol; soluble in acetone and chloroform; and freely soluble in tetrahydrofuran. Its partition coefficient between octanol and water is greater than 5000. Mometasone can exist in various hydrated, crystalline and enantiomeric forms, e.g., as a Monohydrate. This product is available from Schering-Plough Corporation, Kenilworth, N.J. The Mometasone Furoate Monohydrate may be present in amounts of about 0.01 to about 1%, preferably about 0.1%. Other corticosteroids for use in the present invention include Dexamethasone, Butoxicart, Rofleponide, Budesonide, Deflazacort, Ciclesonide, Fluticasone, Beclomethasone, Betamethasone, Fluocinolone, Prednisone, Prednisolone, Loteprednol or Triamcinolone.

This invention further relates to stable formulations containing an antifungally effective amount of the micronized compound represented by the chemical structural formula I:

to, Orbifloxacin, Ciprofloxacin, Danofloxacin, Enoxacin, Grepafloxacin, Levofloxacin, Lomefloxacin, Nalidixic acid, Norfloxacin, Ofloxacin, Sparfloxacin, Marbofloxacin, Enrofloxacin, Ibafloxacin, Garenoxacin, T-3811M1, T-3811M4, T3811M6, Gatifloxacin, Gemifloxacin, Moxifloxacin, Difloxacin, Rufloxacin, Pradofloxacin and Trovafloxacin mesylate and/or metabolites thereof. Other quinolones useful in the practice of the present invention are described in WO 96/16055 published May 30, 1996; U.S. Pat. No. 5,104,868 issued Apr. 14, 1992; U.S. Pat. No. 5,496,947 issued Mar. 5, 1996; U.S. Pat. No. 5,498,615 issued Mar. 12, 1996; U.S. Pat. No. 5,770,597 issued Jun. 23, 1998; U.S. Pat. No. 5,840,333 issued Nov. 24, 1998; U.S. Pat. No. 5,672,600 issued Sep. 30, 1997; U.S. Pat. No. 5,491,139 issued Feb. 13, 1996; U.S. Pat. No. 5,530,116 issued Jun. 25, 1996; and U.S. Pat. No. 5,646,163 issued Jul. 8, 1997, all incorporated by reference herein.

The quinolone compounds useful in the practice of the present invention comprise from about 0.01% to about 30% by weight of the pharmaceutical compositions of the present invention. Preferably, the quinolone compounds useful in the practice of the present invention comprise from about 0.1% to about 10% by weight of the pharmaceutical compositions of the present invention. More preferably, the quinolone compounds useful in the practice of the present invention comprise from about 0.5% to 5% by weight of the pharmaceutical compositions of the present invention.

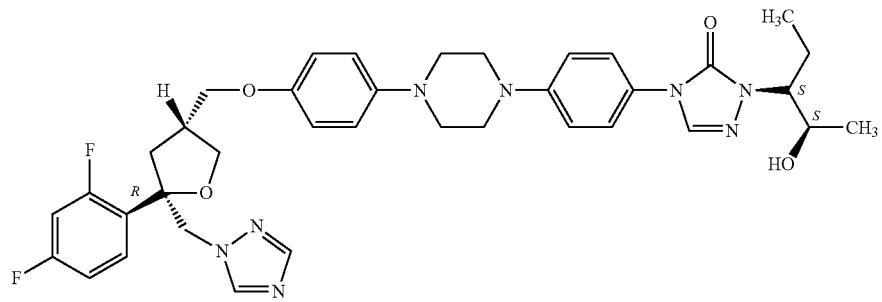

U.S. Pat. No. 5,661,151 discloses the compound of formula I and its potent antifungal activity against a broad range of fungi such as Aspergillis, Candida, Cryptococcus, Fusarium, and other opportunistic fungi. U.S. Pat. Nos. 5,834,472 and 5,846,971, disclose oral pharmaceutical capsule compositions of the compound of structural formula I coated onto inert beads together with a binder. This product is available from Schering-Plough Corporation, Kenilworth, N.J. The Posaconazole may be present in amounts of about 0.01% to about 1%, preferably about 0.11%.

Other triazole anti-fungal compounds for use in the present invention include Voriconazole, Ketoconazole, Fluconazole, Itraconazole, Saperconazole, Neticonazole, Oxiconazole, Isoconazole, Sulconazole, Tercanazole, Tioconazole, and/or the pharmaceutically acceptable salts thereof.

Orbifloxacin is a potent, synthetic broad-spectrum antibacterial agent classified as a quinolone carboxylic acid derivative. It is safe and effective for the management of diseases in dogs and cats associated with bacteria susceptible to Orbifloxacin. Quinolones and derivatives thereof useful in the practice of the present invention include, but are not limited The Orbifloxacin may be present in amounts of about 0.1% to about 10%, preferably about 1%.

Fluorine-containing analogs of antibiotics chloramphenicol and thiamphenicol have been shown to have antibiotic activity, both against organisms sensitive to and resistant to chloramphenicol and thiamphenicol. See Schafer, T. W. et al., "Novel Fluorine-Containing Analogs of Chloramphenicol and Thiamphenicol: Antibacterial and Biological Properties," in CURRENT CHEMOTHERAPY AND INFECTIOUS DISEASE PROCEEDINGS OF THE 11TH ICC AND THE 19TH ICAAC AMERICAN SOCIETY OF MICROBIOLOGY 1980, 444-446. Examples of such compounds, and methods for their manufacture, are described and claimed in U.S. Pat. No. 4,235,892. The medical profession has become increasingly concerned about the transference of bacterial resistance to humans when antibiotics useful in treating humans are administered to livestock. Because the chloramphenicol group of antibiotics is infrequently used now to treat humans, its derivatives are particularly appropriate for veterinary use. Of particular interest are the 3-fluoro, 3-deoxy derivatives.

FORMULA I

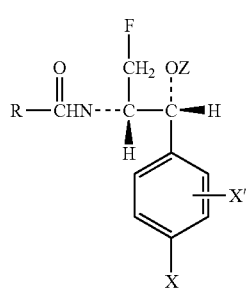

wherein R is a member selected from the group consisting of methyl or ethyl or a halogenated derivative thereof, dihalogenodeuteriomethyl, 1-halogeno-1-deuterioethyl, 1,2-dihalogeno-1-deuterioethyl, azidomethyl and methylsulfonylmethyl;

each of X and X' is a member independently selected from the group consisting of $NO_2$, $SO_2R_1$, $SOR_1$, $SR_1$, $SONH_2$, $SO_2NH_2$, $SONHR_1$, $SO_2NHR_1$, $COR_1$, $OR_1$, $R_1$, CN, halogen, hydrogen, phenyl, and phenyl substituted by halogen, $NO_2$, $R_1$, $OR_1$, $PO_2R_1$, $CONHR_1$, $NHR_1$, $NR_1R_2$, $CONR_1R_2$ or $OCOR_1$, wherein each of $R_1$ and $R_2$ is a member independently selected from the group consisting of methyl, ethyl, n-propyl, isopropyl, butyl, t-butyl, isobutyl and phenyl;

and Z is hydrogen or an acyl group of a hydrocarboncarboxylic acid (preferably a hydrocarbondicarboxylic acid) having up to 16 carbon atoms or an acyl group of an aminohydrocarboncarboxylic acid having up to 12 carbon atoms; and the pharmaceutically acceptable salts of said acyl groups.

Included among the halogenated groups contemplated for the moiety R in Formula I are the mono-, di- and tri-fluoro, the mono-, di- and tri-chloro-, the mono- and di-bromo-, and the iodo-methyl groups as well as the mono- and di-fluoro-, the mono- and di-chloro-, the mono- and di-bromo-, and the iodo-ethyl groups wherein the halogen substituents are preferably on the carbon alpha to the carbonyl function. Also included are mixed dihalogenoalkyl groups in which both halogens are preferably bonded to the carbon alpha to the carbonyl groups, e.g., groups such as fluorochloro-, fluorobromo-, and chlorobromo-methyl and -ethyl, as well as trihalogen-methyl groups such as dichlorofluoro- and difluorochloromethyl.

Also included among the compounds of Formula I are the ester derivatives, e.g. 1-hydrocarboncarboxylates of Formula I wherein Z is an acyl group of a hydrocarboncarboxylic acid having up to 16 carbon atoms that may be saturated, unsaturated, straight chain or branched chain, aliphatic, cyclic, cyclic-aliphatic, aromatic, aryl-aliphatic, or alkyl-aromatic and may be substituted by hydroxy, alkoxy containing from 1 to 5 carbon atoms, carboxyl, $NO_2$, $NHR_1$, $NR_1R_2$, $SR_1$, $SOR_1$, or halogen, wherein $R_1$ and $R_2$ are as defined above.

Other antibacterially active ester derivatives of Formula I are those wherein Z is an acyl group of an amino acid containing up to 12 carbon atoms that may be saturated, unsaturated, straight chain, branched chain or cyclic, that may contain aromatic groups and that may be substituted by hydroxyl groups.

Preferred ester derivatives include those derived from dibasic hydrocarboncarboxylates, e.g. the 1-succinate and 1-palmitate esters, which provide water soluble, pharmaceutically acceptable cationic salts, e.g. the sodium or potassium salts as well as salts with amine, e.g. trimethylamine. Also preferred are ester derivatives of amino acids that provide water soluble, pharmaceutically acceptable acid addition salts with mineral or organic acids, e.g. the hydrochloric, or sulfuric acid, or succinic acid addition salts.

As used herein the term "pharmaceutically acceptable salts" thus includes salts wherein the acidic hydrogen in the dibasic hydrocarboncarboxylate esters of this invention is replaced with a cation (e.g. sodium D-(threo)-1-p-nitrophenyl-2-dichloroacetamido-3-fluoro-1-propyl hemisuccinate) as well as salts wherein the acidic hydrogen forms an acid addition salt with an amine (e.g. D-(threo)-1-p-nitrophenyl-2-dichloroacetamido-3-fluoro-1-propyl hemisuccinate N-trimethylamine salt). Also included are the acid addition salts formed between mineral or organic acids and the amine in the amino acid esters of the compounds of Formula I (e.g. D-(threo)-1-p-nitrophenyl-2-dichloroacetamido-3-fluoro-1-propyl glycinate hydrochloride).

Among the pharmaceutically acceptable cationic salts of the dibasic hydrocarboncarboxylate esters included in Formula I are salts of alkali and alkaline earth metals (e.g., sodium, potassium, calcium, aluminum) and salts with an amine such as trialkylamines, procaine, dibenzylamine, N-benzyl-beta-phenethylamine, N,N'-dibenzylethylenediamine, N-(lower)alkylpiperidines (e.g. N-ethylpiperidine), and N-methyl glucamine.

Preferably R is a halogenated derivative of methyl or ethyl, Z is a hydrogen, X is phenyl, $COR_1$ or $SO_2R_1$, $R_1$ is methyl, and X' is hydrogen. Most preferably R is $CHCl_2$ or $CHF_2$.

A preferred antibiotic compound is florfenicol (D-(threo)-1-p-methylsulfonyl phenyl-2-dichloroacetamido-3-fluoro-1-propanol). Another preferred antibiotic compound is D-(threo)-1-p-methylsulfonyl phenyl-2-difluoroacetamido-3-fluoro-1-propanol. Processes for the manufacture of these preferred antibiotic compounds, and intermediates useful in such processes, are described in U.S. Pat. Nos. 4,311,857; 4,582,918; 4,973,750; 4,876,352; 5,227,494; 4,743,700; 5,567,844; 5,105,009; 5,382,673; 5,352,832; and 5,663,361.

Also preferred antibiotics are tetracyclines. Particularly preferred is chlorotetracycline and oxytetracycline.

Also for use in the present invention are compounds such as Amoxicillin, Ampicillin, Ampicillin Trihydrate, Ampicillin Sodium, Apalcillin, Aspoxicillin, Aziocillin, Bacampicillin, Carbenicillin, Carbenicillin Sodium, Carfecillin, Carindacillin, Ciclacillin, Cloxacillin Sodium, Cloxacillin Benzathine, Dicloxacillin, Dicloxacillin Sodium, Flucloxacillin, Hetacillin, Lenampicillin, Mecillinam, Metampicillin, Methicillin, Meziocillin, Nafcillin, Nafcillin Sodium, Oxacillin, Penicillic Acid, Penicillin G, Penicillin G Benzathine, Penicillin G Potassium, Penicillin G Sodium, Penicillin V, Phenethicillin, Phenethicillin Potassium, Piperacillin, Piperacillin Sodium, Pivampicillin, Sulbenicillin, Sultamicillin, Talampicillin, Ticarcillin, Cefaclor, Cefadroxil, Cefadroxil Monohydrate, Cefamandole, Cefamandole Lithium, Cefamandole Nanfate, Cefamandole Sodium, Cefazaflur, Cefazedone, Cefazolin, Cefazolin Sodium, Cefclidine, Cefdinir, Cefepime, Cefetamet, Cefixime, Cefluprenam, Cefinenoxime, Cefinetazole Sodium, Cefodizime, Cefonicid, Cefoperazone, Cefoperazone Sodium, Ceforanide, Cefoselis, Cefotaxime, Cefotaxime Sodium, Cefotiam, Cefozopran, Cefpimizole, Cefpimizole Sodium, Cefpiramide, Cefpirome, Cefpodoxime, Cefprozil, Cefquinome, Cefroxadine, Cefsulodin, Cefsulodin Sodium Hydrate, Ceftazidime, Ceftazidime Pentahydrate, Ceftezole, Ceftibuten, Ceftiolene, Ceftizoxime, Ceftriaxone, Ceftriaxone Disodium Salt, Ceftriaxone Sodium, Cefuroxime, Cefuzonam, Cephacetrile, Cephalexin, Cephaloridine, Cephalosporin C, Cephalothin, Cephalothin Sodium, Cephapirin, Cephapirin Sodium, Cephradine, Loracarbef, Cefbuperazone, Cefoxitin, Cefoxitin Sodium, Cefminox, Cefinetazole, Cefotetan, either alone or in combination with Beta Lactamase inhibitors such as Clavulanic Acid, Potassium Clavulanate, Sulbactam Lodopenicillanic acid, 6-Bromopenicillanic acid, Olivanic acids, and Tazobactam.

Also for use in the present invention are macrolide antibiotics such as Azithromycin, Brefeldin, Clarithromycin, Erythromycin, Erythromycin Estolate, Erythromycin Ethyl Succinate, Erythromycin Stearate, Josamycin, Kitasamycin and Tulathromycin.

Another preferred antibiotic compound is Tilmicosin. Tilmicosin is a macrolide antibiotic that is chemically defined as 20-dihydro-20-deoxy-20-(cis-3,5-dimethylpiperidin-1-yl)-desmycosin and which is reportedly disclosed in U.S. Pat. No. 4,820,695. Also disclosed in U.S. Pat. No. 4,820,695 is an injectable, aqueous formulation comprising 50% (by volume) propylene glycol, 4% (by volume) benzyl alcohol, and 50 to 500 mg/ml of active ingredient. Tilmicosin may be present as the base or as a phosphate. Tilmicosin has been found to be useful in treatment of respiratory infections, particularly Pasteurella haemolytica infections in cattle when administered by injection over a 4 day treatment period.

Another suitable antibiotic for use in the present invention is Tulathromycin. Tulathromycin has the following chemical structure:

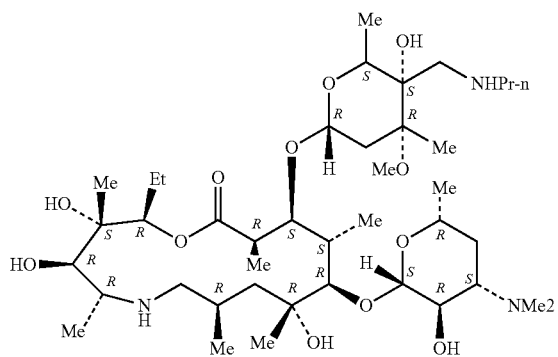

Tulathromycin may be identified as 1-Oxa-6-azacyclopentadecan-15-one, 13-[[2,6-dideoxy-3-C-methyl-3-O-methyl-4-C-[(propylamino)methyl]-α-L-ribo-hexopyranosyl]oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-, (2R, 3S, 4R, 5R, 8R, 10R, 11R, 12S, 13S, 14R). Tulathromycin may be prepared in accordance with the procedures set forth in U.S. Publication No. 2003/0064939 A1, which is incorporated by reference in its entirety. Tulathromycin may be present in injectable dosage forms at concentration levels ranging from about 5.0% to about 70% by weight. Tulathromycin is most desirably administered in dosages ranging from about 0.2 mg per kg body weight per day (mg/kg/day) to about 200 mg/kg/day in single or divided doses (i.e., from 1 to 4 doses per day), and more preferably 1.25, 2.5 or 5 mg/kg once or twice weekly, although variations will necessarily occur depending upon the species, weight and condition of the subject being treated. Tulathromycin may be present in injectable dosage forms at concentration levels ranging from about 5.0% to about 70% by weight.

There are five reasons why this otic product that is intended for use in companion animals is novel. The fluoroquinolone antibiotic (Orbifloxacin) has not been used in this type of product previously (although it is available in Member States in tablet form for the treatment of urinary tract infections in dogs). Moreover, the usual antibiotic in this class of medicines is gentamicin (or other aminoglycosides) which have been associated with an increased incidence of deafness, particularly in dogs. Hence, this product can be expected to have better safety profile.

The anti-inflammatory drug preferably is Mometasone. It is the first in class of corticosteroids. Thus, this product is expected to safer than other topical corticosteroid preparations currently used in veterinary medicine.

The antifungal drug preferably is posaconazole, a drug with 10-400× the antifungal activity of traditional antifungal compounds used in veterinary medicine such as clotrimazole, miconazole, nystatin. It will be the first use of a triazole antifungal in veterinary medicine. The combination for this proposed otic product is new. The product requires only one application per day. In summary, the justification for use of the centralized procedure is:

Novel antibiotic in an otic preparation with none of the ototoxicity of the aminoglycosides often used in such products;
Novel, corticosteroid, with a better safety profile when compared other corticosteroids used in otic preparations;
Potent triazole anti-fungal drug;
Novel combination of the three drugs described above;
Single daily application.

Other inert ingredients can be added to the present composition, as desired. Such ingredients include preservatives, chelating agents, antioxidants and stabilizers. Exemplary preservatives include methyl p-hydroxybenzoate (methylparaben) and propyl p-hydroxybenzoate (propylparaben). Exemplary chelating agents include edetate sodium. Exemplary antioxidants include butylated hydroxyanisole and sodium monothioglycerol.

In order to prepare the suspension compositions of the present invention, the vehicle(s) or a portion of the vehicle(s), are added to the compounding vessel, followed by the remaining excipients and the actives. Additives, such as those listed above, may also be included in the vessel and mixed into the formulation (the order of addition is not critical).

The compositions may be administered once daily or divided into multiple doses. Often only one dose will be sufficient to treat the infection. In some circumstances one dose followed by a second dose 48 hours later will be required to treat the animal. Alternatively, the medication may be administered once daily for up to 7 days. The precise dose will depend on the stage and severity of the infection, the susceptibility of the infecting organism to the composition, and the individual characteristics of the animal species being treated, as will be appreciated by one of ordinary skill in the art.

As stated hereinabove, pharmaceutically-acceptable excipients include, but are not limited to, resins, fillers, binders, lubricants, solvents, glidants, disintegrants, co-solvents, surfactants, preservatives, buffer systems, pharmaceutical-grade dyes or pigments, and viscosity enhancing agents.

Preferred buffer systems include, but are not limited to, NaOH, acetic, boric, carbonic, phosphoric, succinic, malaic, tartaric, citric, benzoic, lactic, glyceric, gluconic, glutaric and glutamic acids and their sodium, potassium and ammonium salts. The pharmaceutical composition of the present invention generally contain from 0.1% to 20% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids.

Preferred preservatives include, but are not limited to, phenol, alkyl esters of parahydroxybenzoic acid, sorbic acid, and methylparaben, o-phenylphenol benzoic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred is sorbic acid. The compositions of the present invention generally include from 0.01% to 5% preservatives.

Preferred viscosity enhancing agents include, but are not limited to, methylcellulose, sodium carboxymethylcellulose, hydroxypropyl-methylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0.1% to 5% viscosity agents.

A particularly preferred thickening agent is Plastibase® 50W: It is available from Bristol-Myers Squibb, Plastibase® 50W contains 5% polyethylene in 95% mineral oil. Polyethylene is an inert hydrocarbon with a high molecular weight and high melting point. It is used as a thickening agent to increase the viscosity of the mineral oil. Other preferred thickening agents include carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Liquid pharmaceutical compositions generally include a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

A preferred class of thickening or gelling or suspending agents includes a class of homopolymers of acrylic acid crosslinked with an alkyl ether of pentaerythritol or an alkyl ether of sucrose, or carbomers. Carbomers are commercially available from B.F. Goodrich as the Carbopol® series. Particularly preferred Carbopols include Carbopol 934, 940, 941, 956, and mixtures thereof. Copolymers of lactide and glycolide monomers, the copolymer having the molecular weight in the range of from about 1,000 to about 120,000 (number average), are useful for delivery of actives. These polymers are described in U.S. Pat. No. 5,198,220, issued Mar. 30, 1993 and U.S. Pat. No. 5,242,910, issued Sep. 7, 1993, both to Damani, and U.S. Pat. No. 4,443,430, to Mattei, issued Apr. 17, 1984.

Thickening agents in an amount from about 0.1% to about 15%, preferably from about 2% to about 10%, more preferably from about 4% to about 8%, by weight of the total composition, can be used. Higher concentrations can be used for sachets, non-abrasive gels and subgingival gels.

The compositions of the present invention may optionally contain lactose, mannitol, sorbitol, tribasic calcium phosphate, dibasic calcium phosphate, compressible sugar, starch, calcium sulfate, dextro and microcrystalline cellulose, magnesium stearate, stearic acid, talc, colloidal silicon dioxide, starch, sodium starch glycolate, crospovidone, croscarmelose sodium, and microcrystalline cellulose, acacia, tragacanth, hydroxypropylcellulose, pregelantinized starch, gelatin, povidone, ethylcellulose, hydroxypropylcellulose, hydroxypropylmethylcellulose, and methylcellulose.

The present invention is more particularly described in the following example which are intended as illustrative only since numerous modifications and variations therein will be apparent to those skilled in the art.

EXAMPLE 1

| Ingredient | mg/g |
|---|---|
| Orbifloxacin micronized | 10.0* |
| Mometasone Furoate Monohydrate micronized | 1.0** |
| Posaconazole micronized | 1.0*** |
| Mineral Oil USP (40 Centistokes) | 685.0 |
| Plasticized Hydrocarbon Gel - Ointment Base (Plastibase 50W) | q.s. to 1.0 g**** |

The actual amount of Orbifloxacin is to be determined based on assay and moisture content of the lot to be used. The actual amount of Mometasone Furoate Monohydrate is to be determined based on assay and moisture content of the lot to be used. The actual amount of Posaconazole is to be determined based on assay and moisture content of the lot to be used. The formulation may be prepared as known to one of ordinary skill in the art.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. A topical pharmaceutical composition for the effective treatment of an otic infection in an animal without enhancing the incidence of deafness in the treated animal, wherein:
    the composition comprises:
        Orbifloxacin or one of its pharmaceutically acceptable salts in an amount of about 0.1% to about 10% by weight,
        Posaconazole in an amount of about 0.01% to about 1% by weight,
        Mometasone Furoate Monohydrate in an amount of about 0.01% to about 1% by weight,
    a viscosity enhancing agent in an amount of about 0.1% to about 5% by weight and
        at least one pharmaceutically acceptable carrier; wherein the composition is a suspension.

2. The composition according to claim 1, wherein at least about 0.01% of the composition is the Mometasone Furoate Monohydrate.

3. The composition according to claim 1, wherein at least about 0.1% of the composition is the Orbifloxacin.

4. The composition according to claim 1, wherein at least about 0.01% of the composition is Posaconazole.

5. The composition according to claim 1, wherein the composition is in a single daily dosage form.

6. The composition according to claim 1, comprising a viscosity enhancing agent selected from the group consisting of methylcellulose, water soluble salts of cellulose ethers, carboxymethyl hydroxyethyl cellulose, hydroxyethyl cellulose, sodium carboxymethylcellulose, hydroxypropylmethylcellulose, hydroxypropylcellulose, sodium alginate, carbomer, providone, acacia, guar gum, xanthan gum, gum karaya, gum arabic, gum tragacanth, magnesium aluminum silicate, carboxyvinyl polymers, carrageenen, laponite, and mineral oil with polyethylene.

7. The composition according to claim 1, wherein at least about 0.1 wt % of the composition is the Mometasone Furoate Monohydrate.

8. The composition according to claim 1, wherein at least about 1 wt % of the composition is the Orbifloxacin.

9. The composition according to claim 1, wherein at least about 0.1 wt % of the composition is Posaconazole.

10. The composition according to claim 1, wherein the composition comprises:
   Orbifloxacin or one of its pharmaceutically acceptable salts in an amount of about 1% by weight,
   Posaconazole in an amount of about 0.1% by weight,
   Mometasone Furoate Monohydrate in an amount of about 0.1% by weight,
   a viscosity enhancing agent comprising mineral oil and polyethylene in an amount of about 0.1% to about 5% by weight and
   at least one pharmaceutically acceptable carrier; and wherein
   the composition is a suspension.

* * * * *